(12) United States Patent
Deng et al.

(10) Patent No.: US 9,273,131 B2
(45) Date of Patent: Mar. 1, 2016

(54) ANTI-BFGF HUMANIZED DOUBLE-STRANDED ANTIBODY WITH STABLE DISULFIDE BOND, PREPARATION METHOD AND APPLICATION THEREOF

(75) Inventors: Ning Deng, Guangzhou (CN); Haowu Jiang, Guangzhou (CN); Zhongkui Kang, Guangzhou (CN); Hong Wang, Guangzhou (CN); Qifang Song, Guangzhou (CN)

(73) Assignee: Jinan University (CN)

( * ) Notice: Subject to any disclaimer, the term of this patent is extended or adjusted under 35 U.S.C. 154(b) by 0 days.

(21) Appl. No.: 14/369,363

(22) PCT Filed: Aug. 20, 2012

(86) PCT No.: PCT/CN2012/080357
§ 371 (c)(1),
(2), (4) Date: Jun. 27, 2014

(87) PCT Pub. No.: WO2013/097470
PCT Pub. Date: Jul. 4, 2013

(65) Prior Publication Data
US 2014/0350225 A1  Nov. 27, 2014

(30) Foreign Application Priority Data
Dec. 28, 2011 (CN) .......................... 2011 1 0450855

(51) Int. Cl.
*C07K 16/22* (2006.01)
*A61K 39/395* (2006.01)
*C12N 15/66* (2006.01)

(52) U.S. Cl.
CPC ............... *C07K 16/22* (2013.01); *A61K 39/395* (2013.01); *C12N 15/66* (2013.01); *C07K 2317/31* (2013.01); *C07K 2317/622* (2013.01); *C07K 2317/626* (2013.01)

(58) Field of Classification Search
None
See application file for complete search history.

(56) References Cited

FOREIGN PATENT DOCUMENTS

| CN | 101367876 A | 2/2009 |
|---|---|---|
| CN | 102532319 A | 7/2012 |

OTHER PUBLICATIONS

Chen, Yuping et al., Construction and expression of disulphide stabilized bispecific diabody, Journal of Peking University (Health Sciences), Feb. 2002, vol. 34, No. 1, pp. 39-42, p. 40, section 1.3, English translation of Abstract provided.

Wang, Hong et al., Cloning of the variable region genes from hybridoma against bFGF and expression of single chain antibody fragments in *E. coli* HB2151, Chinese Journal of Cellular and Molecular Immunology, 2007, vol. 23, No. 12, pp. 1150-1153, p. 1151, paragraph 1, English translation of Abstract provided.

*Primary Examiner* — Marianne P Allen
(74) *Attorney, Agent, or Firm* — Lerner, David, Littenberg, Krumholz & Mentlik, LLP (57) ABSTRACT

Disclosed are an anti-bFGF humanized double-stranded antibody with stable disulfide bond, the preparation method and the applications thereof. The amino acid sequence of the anti-bFGF humanized ds-Diabody is shown in SEQ ID NO.1. The nucleotide sequence of gene encoding the anti-bFGF humanized ds-Diabody is shown in SEQ ID NO.2. By site-directed mutation, two cysteine residues are introduced into VL and VH domain of anti-bFGF Diabody, thus introducing the disulfide bond and form ds-Diabody. It is shown by experiments that the obtained ds-Diabody has the following advantages: enhanced stability; better affinity when binding to the specific antigen bFGF; moderate relative molecular weight, good tumor targeting, more powerful in tumor tissue penetration, and higher blood clearance rate, showing a broad application prospects in the clinic diagnosis and tumor therapy.

6 Claims, 3 Drawing Sheets

SEQUENCE LISTING

<160> NUMBER OF SEQ ID NOS: 13

<210> SEQ ID NO 1
<211> LENGTH: 235
<212> TYPE: PRT
<213> ORGANISM: artificial sequence
<220> FEATURE:
<223> OTHER INFORMATION: Anti-bFGF humanized ds-Diabody

<400> SEQUENCE: 1

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Cys Gly Thr Lys Leu Thr Val Leu Gly Gly
                100                 105                 110

Gly Gly Ser Gln Val Gln Leu Gln Glu Ser Gly Gly Gly Leu Val Gln
            115                 120                 125

Pro Gly Gly Ser Leu Arg Leu Ser Cys Ala Ala Ser Gly Phe Thr Phe

Ser Ser Tyr Glu Met Asn Trp Val Arg Gln Ala Pro Gly Lys Cys Leu
145                 150                 155                 160

Glu Trp Val Ser Tyr Ile Ser Ser Gly Ser Thr Ile Tyr Tyr Ala
            165                 170                 175

Asp Ser Val Lys Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Arg Glu Leu Thr Gly Asp Trp Gly Ala Phe Asp Ile
    210                 215                 220

Trp Gly Gln Gly Thr Met Val Thr Val Ser Ser
225                 230                 235

<210> SEQ ID NO 2
<211> LENGTH: 705
<212> TYPE: DNA
<213> ORGANISM: artificial sequence
<220> FEATURE:
<223> OTHER INFORMATION: Nucleotide sequence encoding said anti-bFGF humanized ds-Diabody

<400> SEQUENCE: 2
cagtctgtgt tgacgcagcc tgcctccgtg tctgggtctc ctggacaatc gatcaccatc     60
tcctgcactg gaaccagcag tgacgttggt ggttataact atgtctcctg gtaccaacaa    120
cacccaggca aagcccccaa actcatgatt tatgatgtca gtaatcggcc ctcagggggtt   180 tctaatcgct tctctggctc caagtctggc aacacggcct ccctgaccat ctctgggctc    240
caggctgagg acgaggctga ttattactgc agctcatata caagcagcag cactgtggta    300
ttcggctgtg ggaccaagct gaccgtccta ggtggcggtg gctcgcaggt gcagctgcag    360
gagtctgggg gaggcttggt acagcctgga gggtccctga gactctcctg tgcagcctct    420
ggattcacct tcagtagtta tgaaatgaac tgggtccgcc aggctccagg gaagtgtctg    480
gagtgggttt catacattag tagtagtggt agtaccatat actacgcaga ctctgtgaag    540
ggccggttca ccatctccag agacaacgcc aagaactcac tgtatctgca aatgaacagc    600
ctgagagccg aggacacggc tgtgtattac tgtgcgagag agctaactgg ggattggggt    660
gcttttgata tctggggcca ggggacaatg gtcactgtct cctca                    705

<210> SEQ ID NO 3
<211> LENGTH: 360
<212> TYPE: DNA
<213> ORGANISM: artificial sequence
<220> FEATURE:
<223> OTHER INFORMATION: genes encoding a heavy chain variable region

<400> SEQUENCE: 3
caggtgcagc tgcaggagtc tgggggaggc ttggtacagc ctggagggtc cctgagactc     60
tcctgtgcag cctctggatt caccttcagt agttatgaaa tgaactgggt ccgccaggct    120
ccagggaagg gctgagtg gtttcatac attagtagta gtggtagtac catatactac    180
gcagactctg tgaagggccg gttcaccatc tccagagaca cgccaagaa ctcactgtat    240 ctgcaaatga acagcctgag agccgaggac acggctgtgt attactgtgc gagagcta    300 actggggatt ggggtgcttt tgatatctgg ggccagggga caatggtcac tgtctcctca    360

<210> SEQ ID NO 4

<211> LENGTH: 333
<212> TYPE: DNA
<213> ORGANISM: artificial sequence
<220> FEATURE:
<223> OTHER INFORMATION: genes encoding a light chain variable region

<400> SEQUENCE: 4

```
cagtctgtgt tgacgcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgatgtca gtaatcggcc ctcagggggtt    180
tctaatcgct tctctggctc caagtctggc aacacggcct ccctgaccat ctctgggctc     240
caggctgagg acgaggctga ttattactgc agctcatata caagcagcag cactgtggta     300
ttcggcggag ggaccaagct gaccgtccta ggg                                  333
```

<210> SEQ ID NO 5
<211> LENGTH: 29
<212> TYPE: DNA
<213> ORGANISM: artificial sequence
<220> FEATURE:
<223> OTHER INFORMATION: Primer 1

<400> SEQUENCE: 5

```
gcggccgccc agtctgtgtt gacgcagcc                                        29
```

<210> SEQ ID NO 6
<211> LENGTH: 45
<212> TYPE: DNA
<213> ORGANISM: artificial sequence
<220> FEATURE:
<223> OTHER INFORMATION: Primer 2

<400> SEQUENCE: 6

```
taggacggtc agcttggtcc cacagccgaa taccacagtg ctgct                      45
```

<210> SEQ ID NO 7
<211> LENGTH: 35
<212> TYPE: DNA
<213> ORGANISM: artificial sequence
<220> FEATURE:
<223> OTHER INFORMATION: Primer 3

<400> SEQUENCE: 7

```
cgagccaccg ccacctagga cggtcagctt ggtcc                                 35
```

<210> SEQ ID NO 8
<211> LENGTH: 36
<212> TYPE: DNA
<213> ORGANISM: artificial sequence
<220> FEATURE:
<223> OTHER INFORMATION: Primer 4

<400> SEQUENCE: 8

```
ggtggcggtg gctcgcaggt gcagctgcag gagtct                                36
```

<210> SEQ ID NO 9
<211> LENGTH: 33
<212> TYPE: DNA
<213> ORGANISM: artificial sequence
<220> FEATURE:
<223> OTHER INFORMATION: Primer 5

<400> SEQUENCE: 9

```
cccactccag acacttccct ggagcctggc gga                                   33
```

```
<210> SEQ ID NO 10
<211> LENGTH: 33
<212> TYPE: DNA
<213> ORGANISM: artificial sequence
<220> FEATURE:
<223> OTHER INFORMATION: Primer 6

<400> SEQUENCE: 10
tccagggaag tgtctggagt gggtttcata cat                            33

<210> SEQ ID NO 11
<211> LENGTH: 45
<212> TYPE: DNA
<213> ORGANISM: artificial sequence
<220> FEATURE:
<223> OTHER INFORMATION: Primer 7

<400> SEQUENCE: 11
ggatcctcaa tgatgatgat gatggtgtga ggagacagtg accat                45

<210> SEQ ID NO 12
<211> LENGTH: 23
<212> TYPE: DNA
<213> ORGANISM: artificial sequence
<220> FEATURE:
<223> OTHER INFORMATION: Upstream primer for ScFv amplification

<400> SEQUENCE: 12
ggatcccagg tgcagctgca gga                                       23

<210> SEQ ID NO 13
<211> LENGTH: 22
<212> TYPE: DNA
<213> ORGANISM: artificial sequence
<220> FEATURE:
<223> OTHER INFORMATION: Downstream primer for ScFv amplification

<400> SEQUENCE: 13
aagcttgctg accgtcctag gg                                        22
```

ANTI-BFGF HUMANIZED DOUBLE-STRANDED ANTIBODY WITH STABLE DISULFIDE BOND, PREPARATION METHOD AND APPLICATION THEREOF

CROSS-REFERENCE TO RELATED APPLICATIONS

The present application is a national phase entry under 35 U.S.C. §371 of International Application No. PCT/CN2012/080357 filed on Aug. 20, 2012, published in Chinese, which claims the benefit of China Patent Application No. 201110450855.0 filed Dec. 28, 2011, the disclosure of which is hereby incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 26, 2014, is named 9WANHU-2 Sequence Listing_ST25.txt and is 6,539 bytes in size.

FIELD OF THE INVENTION

The present invention belongs to the field of antibodies, relating to a dimeric antibody, especially an anti-bFGF humanized diabody with stable disulfide bond, preparation method and usage thereof.

BACKGROUND OF THE INVENTION

Basic Fibroblast Growth Factor (bFGF) is the basic Fibroblast Growth Factor, and is a broadly presented mitogen, which can promote the effect of proliferation, differentiation and anti-apoptosis of many kinds of cells including tumor cells and vascular endothelial cells by means of autocrine or paracrine. bFGF has various kinds of biological effects, including growth promoting, dividing and differentiating, and it has a strong proliferation promoting effect for fibroblast. A growing number of studies have indicated that bFGF is highly expressed in many kinds of tumor tissues and is closely related to the occurrence and development of tumors. Therefore, bFGF could be a good target for tumor medical treatment. It is also considered as an effective method for tumor therapy by neutralizing bFGF with antibodies and preventing its binding with the receptors.

The clinical study of therapeutic monoclonal antibody has lasted for more than thirty years, and there are more than 400 kinds of therapeutic monoclonal antibodies enter into the clinical stage with commercial support. Nowadays, monoclonal antibodies have been established as a key way for medical treatment directed to varied diseases. In 1995, the first mouse-source monoclonal antibody Edrecolomab was approved in Germany, which was groundbreaking. However, when this mouse-source antibody was applied to human bodies, as a foreign protein, immune response directed to the foreign protein was induced and anti-mouse antibodies (HAMA) were produced. The subsequent studies have demonstrated that this antibody therapy was not as effective as the standard medical treatment. As a result, Edrecolomab exit the market finally. With the development of the molecular biological technology and the clarification of the structure of antibodies, the technology of DNA recombination was applied to modify the antibody, and many kinds of gene engineered antibodies emerged. The initial gene engineered antibodies, including human-mouse chimeric antibodies and remodel antibodies, were for humanized modification in order to decrease the heterogeneity of mouse-monoclonal antibody. The former one was easy to operate but with lower degree of humanization; the latter one was technically difficult but with higher degree of humanization. The appearance of technologies of antibody library have provided new solutions for humanization, however, more mature technologies are required. After that, in order to improve the property of antibodies, various kinds of products such as small molecular antibodies and antibody fusion protein have appeared. Where the small molecular antibodies, as the fragments of the antibody molecules with the function of antigen binding, have the advantages of small molecular weight and strong penetrating ability, and are easy to be constructed and expressed.

Double-stranded antibody (Diabody) is a kind of small molecular antibody, constructed based on the single-stranded antibody, with the characteristics of moderate molecular weight and bivalent state, and is one of the best tumor targeting antibodies. It is also characterized with high penetration ability for tumor tissue and moderate blood clearance rate. Disulfide bond stabilized-diabody (ds-Diabody) is a stable Diabody formed on the basis of Diabody by introducing disulfide bond. Stability of the ds-Diabody is improved, and thus a broadened application perspective is presented. Up to now, there was no paper or patent report about anti-bFGF humanized ds-Diabody.

SUMMARY OF THE INVENTION

In order to overcome the disadvantages and shortages in the art, the primary purpose of the present invention is to provide an anti-bFGF humanized ds-Diabody. The anti-bFGF humanized ds-Diabody has two antigen-binding sites, and is a bivalent antibody with a better affinity; by site-directed mutation, two cysteine residues are introduced to introduce the disulfide bond, and thus the ds-Diabody is formed, allowing the two peptide chains to covalently bonded, bringing a highly improved stability.

Another purpose of the invention is to provide a preparation method of said anti-bFGF humanized ds-Diabody.

Yet another purpose of the invention is to provide applications of said anti-bFGF humanized ds-Diabody.

The purpose of the invention is achieved by the following technology: an anti-bFGF humanized ds-Diabody with an amino acid sequence (SEQ ID NO:1) as below:

QSVLTQPASVSGSPGQSITISCTGTSSDVGGYNYVSWYQQHPGKAPKLMI

YDVSNRPSGVSNRFSGSKSGNTASLTISGLQAEDEADYYCSSYTSSSTVV

FGCGTKLTVLGGGGSQVQLQESGGGLVQPGGSLRLSCAASGFTFSSYEMN

WVRQAPGKCLEWVSYISSSGSTIYYADSVKGRFTISRDNAKNSLYLQMNS

LRAEDTAVYYCARELTGDWGAFDIWGQGTMVTVSS;

Nucleotide sequence encoding said anti-bFGF humanized ds-Diabody (SEQ ID NO:2) is shown as below:

CAGTCTGTGTTGACGCAGCCTGCCTCCGTGTCTGGGTCTCCTGGACAATC

GATCACCATCTCCTGCACTGGAACCAGCAGTGACGTTGGTGGTTATAACT

ATGTCTCCTGGTACCAACAACACCCAGGCAAAGCCCCCAAACTCATGATT

TATGATGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

-continued

ACGAGGCTGATTATTACTGCAGCTCATATACAAGCAGCAGCACTGTGGTA

TTCGGCTGTGGGACCAAGCTGACCGTCCTAGGTGGCGGTGGCTCGCAGGT

GCAGCTGCAGGAGTCTGGGGGAGGCTTGGTACAGCCTGGAGGGTCCCTGA

GACTCTCCTGTGCAGCCTCTGGATTCACCTTCAGTAGTTATGAAATGAAC

TGGGTCCGCCAGGCTCCAGGGAAGTGTCTGGAGTGGGTTTCATACATTAG

TAGTAGTGGTAGTACCATATACTACGCAGACTCTGTGAAGGGCCGGTTCA

CCATCTCCAGAGACAACGCCAAGAACTCACTGTATCTGCAAATGAACAGC

CTGAGAGCCGAGGACACGGCTGTGTATTACTGTGCGAGAGAGCTAACTGG

GGATTGGGGTGCTTTTGATATCTGGGGCCAGGGGACAATGGTCACTGTCT

CCTCA;

Sequence encoding said anti-bFGF humanized ds-Diabody, is on the basis of genes encoding a light chain variable region ($V_L$) and a heavy chain variable region ($V_H$) of the humanized anti-bFGF scFv antibody that two of them will further form the ds-Diabody. By overlapping PCR, the amino acid Gly at the $100^{th}$ position of $V_L$ and the amino acid Gly at the $44^{th}$ position of $V_H$ are site-directed mutated to Cys, introducing the covalent bond of disulfide bond, and simultaneously, a gene encoding a linker peptide (amino acid sequence is GGGGS) is used to link the mutated light and the heavy chain variable region to construct the gene fragment $V_L$-GGGGS-$V_H$. It is recombined with eukaryotic expression vector (p3XFLAG-Myc-CMV-25, Sigma-Aldrich Co.), then a covalent disulfide bond will be formed within the Diabody molecules expressed in the human embryonic kidney cells (293T cell), to form the ds-Diabody.

Gene sequence encoding the heavy chain variable region ($V_H$) of said humanized anti-bFGF scFv antibody (SEQ ID NO:3) is shown as below:

CAGGTGCAGCTGCAGGAGTCTGGGGGAGGCTTGGTACAGCCTGGAGGGTC

CCTGAGACTCTCCTGTGCAGCCTCTGGATTCACCTTCAGTAGTTATGAAA

TGAACTGGGTCCGCCAGGCTCCAGGGAAGGGGCTGGAGTGGGTTTCATAC

ATTAGTAGTAGTGGTAGTACCATATACTACGCAGACTCTGTGAAGGGCCG

GTTCACCATCTCCAGAGACAACGCCAAGAACTCACTGTATCTGCAAATGA

ACAGCCTGAGAGCCGAGGACACGGCTGTGTATTACTGTGCGAGAGAGCTA

ACTGGGGATTGGGGTGCTTTTGATATCTGGGGCCAGGGGACAATGGTCAC

TGTCTCCTCA;

Gene sequence encoding the light chain variable region ($V_L$) of said humanized anti-bFGF scFv antibody (SEQ ID NO:4) is shown as below:

CAGTCTGTGTTGACGCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAACACCCAGGCAAAGCCCCCAAACTCATGATT

TATGATGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGCAGCAGCACTGTGGTA

TTCGGCGGAGGGACCAAGCTGACCGTCCTAGGG;

A preparation method of the anti-bFGF humanized ds-Diabody comprises the following steps:

(1) The $V_L$ gene fragment and the $V_H$ gene fragment encoding the anti-bFGF single-stranded antibody (screened from a phage antibody library) are used as templates. The amino acid Gly at the $100^{th}$ position of the antibody VL and the amino acid Gly at the $44^{th}$ position of the antibody VH are site-directed mutated to Cys by overlapping PCR and PCR. The light chain variable region and the heavy chain variable region are linked by a gene fragment of a linker peptide. A gene fragment encoding $V_L$-GGGGS-$V_H$ is constructed;

(2) The gene fragment of $V_L$-GGGGS-$V_H$ obtained by step (1) is cloned into a eukaryotic expression vector to be expressed, and after purification, the anti-bFGF humanized ds-Diabody is obtained.

The nucleotide sequence of the $V_H$ gene described in step (1) (SEQ ID NO:3) is shown as below:

CAGGTGCAGCTGCAGGAGTCTGGGGGAGGCTTGGTACAGCCTGGAGGGTC

CCTGAGACTCTCCTGTGCAGCCTCTGGATTCACCTTCAGTAGTTATGAAA

TGAACTGGGTCCGCCAGGCTCCAGGGAAGGGGCTGGAGTGGGTTTCATAC

ATTAGTAGTAGTGGTAGTACCATATACTACGCAGACTCTGTGAAGGGCCG

GTTCACCATCTCCAGAGACAACGCCAAGAACTCACTGTATCTGCAAATGA

ACAGCCTGAGAGCCGAGGACACGGCTGTGTATTACTGTGCGAGAGAGCTA

ACTGGGGATTGGGGTGCTTTTGATATCTGGGGCCAGGGGACAATGGTCAC

TGTCTCCTCA;

The nucleotide sequence of the $V_L$ gene described in step (1) (SEQ ID NO:4) is shown as below:

CAGTCTGTGTTGACGCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAACACCCAGGCAAAGCCCCCAAACTCATGATT

TATGATGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGCAGCAGCACTGTGGTA

TTCGGCGGAGGGACCAAGCTGACCGTCCTAGGG;

Step (1) is preferably as below:
(1) Primer Design:

```
Primer 1:
5'-GCGGCCGCCCAGTCTGTGTTGACGCAGCC-3';
(SEQ ID NO: 5)

Primer 2:
5'-TAGGACGGTCAGCTTGGTCCCACAGCCGAATACCACAGTG
CTGCT-3'; (SEQ ID NO: 6)

Primer 3:
5'-CGAGCCACCGCCACCTAGGACGGTCAGCTTGGTCC-3';
(SEQ ID NO: 7)

Primer 4:
5'-GGTGGCGGTGGCTCGCAGGTGCAGCTGCAGGAGTCT-3';
(SEQ ID NO: 8)

Primer 5:
5'-CCCACTCCAGACACTTCCCTGGAGCCTGGCGGA-3';
(SEQ ID NO: 9)
```

```
Primer 6:
5'-TCCAGGGAAGTGTCTGGAGTGGGTTTCATACAT-3';
(SEQ ID NO: 10)

Primer 7:
5'-GGATCCTCAATGATGATGATGATGGTGTGAGGAGACAGTG
ACCAT-3'; (SEQ ID NO: 11)
```

(2) The Amino Acid Gly at the $100^{th}$ Position of $V_L$ is Site-Directed Mutated to Cys by PCR, and the Gene Fragment $V_L$-GGGGS is Obtained by Amplification:

A. The $V_L$ gene fragment and the $V_H$ gene fragment encoding the anti-bFGF single-stranded antibody are used as the templates. The $V_L$ in which the amino acid at the $100^{th}$ position is mutated from Gly to Cys is obtained by PCR amplification with the primer 1 (SEQ ID NO:5) and primer 2 (SEQ ID NO:6);

B. By using the product obtained from step A as the template, the gene fragment of $V_L$-GGGGS is obtained by PCR amplification with the primer 1 (SEQ ID NO:5) and primer 3 (SEQ ID NO:7);

(3) The Amino Acid at the $44^{th}$ Position of $V_H$ is Site-Directed Mutated from Gly to Cys by PCR. The Gene Fragment of $V_H$-GGGGS is Obtained by Amplification:

C. The $V_L$ gene fragment and the $V_H$ gene fragment encoding the anti-bFGF single-stranded antibody are used as the templates. The $V_H$-GGGGS in which the amino acid Gly at the $44^{th}$ position is mutated to Cys is obtained by PCR amplification with primer 4 (SEQ ID NO:8) and primer 5 (SEQ ID NO:9);

D. The $V_L$ gene fragment and the $V_H$ gene fragment encoding the anti-bFGF single-stranded antibody are used as the templates. The $V_H$-GGGGS with BamHI site is obtained by PCR amplification with primer 6 (SEQ ID NO:10) and primer 7 (SEQ ID NO:11);

E. The product obtained from step C and step D are spliced to obtain the splicing product; then the splicing product and primer 4 and 7 as the templates are used as the templates, and the complete $V_H$-GGGGS is obtained by PCR amplification.

(4) PCR splicing, and gene fragment $V_L$-GGGGS-$V_H$ amplifying: the products obtained from step (2) and step (3) are spliced to obtain the splicing product; then the splicing product is used as the template, the complete $V_L$-GGGGS-$V_H$ is obtained by PCR amplification with primer 1 (SEQ ID NO:5) and primer 7 (SEQ ID NO:11).

Preferably, the eukaryotic expression vector of step (2) is p3XFLAG-Myc-CMV-25.

Usage of the above mentioned anti-bFGF humanized ds-Diabody in the preparation of anti-tumor therapy.

The present invention has the following advantages and effects compared with prior art:

(1) bFGF is humanized protein, which would not induce human immune response, and it is related closely with tumors, thus it cannot be used directly to develop vaccine. However, as a fully humanized antibody, the anti-bFGF humanized ds-Diabody prepared in the present invention can solve the problems of HAMA reactions which is unavoidable caused by mouse-source monoclonal antibody, and thus can be developed directly for human medical treatment.

(2) The anti-bFGF humanized ds-Diabody prepared by the present invention is a dimer formed by two single-stranded antibodies covalently bonded by disulfide bond, comprising two antibody-binding sites, and is bivalent, with good affinity. In addition, disulfide bond is introduced into the ds-Diabody, allowing the two peptide chains to bind by covalent bond, largely increasing the stability of the antibody. Moreover, the ds-Diabody has a moderate relative molecular weight, good tumor targeting ability, approved tumor tissue penetrating power and higher bold clearance rate, showing a broad application prospects in the clinic diagnosis and medical treatment.

BRIEF DESCRIPTION OF THE DRAWINGS

Lane M is the nucleic acid molecular weight marker; lane 1 is the site-directed mutated ds-Diabody gene fragment obtained by PCR amplification.

Lane $M_1$ and lane $M_2$ are the nucleotide molecular weight markers respectively; lane 1 is the result of double enzyme digestion of the expression vector p3XFLAG-Myc-CMV-25-ds-Diabody.

Lane 1 is the Western blot assay of the ds-Diabody in cell expression supernatant that has been subjected to SDS-PAGE under non-reducing condition; lane 2 is the Western blot assay of the ds-Diabody in cell expression supernatant that has been subjected to SDS-PAGE under reducing condition.

Lane M is the protein molecular weight marker; lane 1 is the purified anti-bFGF humanized ds-Diabody.

DETAILED DESCRIPTION

The present invention will be further described in detail below with the combination of the examples and the figures; the embodiment of the present invention is not limited thereto.

Example 1

Preparation of the $V_L$ Gene Fragment and the $V_H$ Gene Fragment Encoding the Anti-bFGF Single-Stranded Antibody (1) The Screening of the Antibody Library of Phage Firstly, the bFGF (Beijing Qi Wei Yi Cheng Co.) was diluted to 50~100 μg/ml by 0.05 mol/L, pH8.7 carbonate buffer solution, and then 1 mL of the diluted bFGF was used to coate the immunotube (Immunotube, NUNC Co.), which is then kept overnight at 4° C. In the next day, the immunotube was filled with 2.5% (m/v) fat-free milk powder at 37° C., blocked for 2 h, and then the blocked solution therein was drained off. After that, 1 mL phage antibody library (about $10^{13}$ CFU) (Enprobiotech Co.) is added and incubated at 37° C. for 2 h. Then the phage antibody solution was adsorbed, and washed twice with the PBS (0.01M, pH7.2) containing 0.05% (v/v) Twain 20, (washed ten times for the second round, then washed more than 20 times for further selection), washed once with distilled water.

Then, the phage antibody bound to the solid phase was recycled with two methods: (1) 1 ml of fresh XL1-Blue bacterium (Beijing Ding Guo Chang Sheng BioTech Inc.) was added, incubated at 37° C. for 15 minutes and then transferred into 10 ml SB medium (every 1 liter medium comprises 309 g tryptone, 209 g yeast extracts and 19 g of MoPs, with a pH value of 7.0) containing 20 μg/ml Amp (Ampicillinum) and 10 μg/ml of Tet (tetracycline); (2) The recycled bacterial infected immunotube was washed twice with distilled water, and 1 ml eluent (0.1 ml HCl, adjusted to pH=2.2 with glycine, then added with BSA to 0.1%(m/v)) was added, stayed still at 37° C. for 15 minutes, then recycled by elution. After exsuction of the eluent, 40 μL 2 mol/L Tris solution was added immediately to neutralize, then 10 ml of XL1-Blue cell (OD600=0.8) was added, and then stayed still for 15 minutes at 37° C. After that, 10 ml SB medium comprising 20 μg/ml Amp and 10 μg/ml Tet was added. Some of the recycled bacterium solution above were taken out and added to the plates to measure CFU. The rest bacteria were cultured at 37° C. for 3 h, expanded to achieve a volume of 50 ml, and then $1.7 \times 10^{12}$ PFU helper virus VCSM13 (Guan Zhou Ying Wei Chuang Jin Biotech Inc.) were added, shaken cultured at 30° C. overnight. The supernatant was then recovered the next day, routinely PEG precipitated, and the obtained secondary phage antibody library can be ready for the next round of screening. Three rounds of screening were carried out according to the same methods, to obtain scFv antibody clone of positive phage.

(2) Preparation of the Phage Antibody and Detection of Specificity of Anti-bFGF

The colonies were randomly selected from the $4^{th}$ round screened plates and transferred into the 2YT liquid medium comprising 50 μg/mL Amp and cultured at 37° C. overnight, then 30 μL bacterium was transferred to 1 mL LB culture medium at the next day, and cultured to logarithm growth phase at 37° C. The helper viruses VCSM13 were added and cultured overnight at 30° C. The supernatant was collected. ELISA test was carried out according to the procedure as below: The antigen (i.e. bFGF) was diluted to 10 μg/ml. The ELISA plates were coated with 50 μL diluted antigen, and the liquid in the well thereof was discarded after 2 h, then the plates were blocked with 3% (w/v) fat-free milk—PBS solution (i.e. using 0.01M, pH7.2 PBS prepared fat-free milk solution), then after blocking phage antibody liquid (i.e. the positive phage obtained by the third round screening) is added, incubated at 37° C. for 1 h. Then, they were washed for three times with 0.05% (w/v) Tween 20—PBS solution (i.e. with the PBS prepared fat-free milk solution of 0.01M, pH7.2), and added with HRP-anti M13 mouse monoclonal antibody (Promega Co.) to conduct reaction. Then after washing, they were stained by TMB substrate and detected at A450. The specific phage antibody clones binding to bFGF were selected. By sequencing, the genes which encoding the humanized scFv antibody against human basic Fibroblast Growth Factor were obtained.

Gene sequence encoding the heavy chain variable region ($V_H$ gene) (SEQ ID NO:3) is shown as below:

CAGGTGCAGCTGCAGGAGTCTGGGGGAGGCTTGGTACAGCCTGGAGGGTC

CCTGAGACTCTCCTGTGCAGCCTCTGGATTCACCTTCAGTAGTTATGAAA

TGAACTGGGTCCGCCAGGCTCCAGGGAAGGGGCTGGAGTGGGTTTCATAC

ATTAGTAGTAGTGGTAGTACCATATACTACGCAGACTCTGTGAAGGGCCG

GTTCACCATCTCCAGAGACAACGCCAAGAACTCACTGTATCTGCAAATGA

ACAGCCTGAGAGCCGAGGACACGGCTGTGTATTACTGTGCGAGAGAGCTA

ACTGGGGATTGGGGTGCTTTTGATATCTGGGGCCAGGGGACAATGGTCAC

TGTCTCCTCA;

Gene sequence encoding the light chain variable region ($V_L$ gene) (SEQ ID NO:4) is shown as below:

CAGTCTGTGTTGACGCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAACACCCAGGCAAAGCCCCCAAACTCATGATT

TATGATGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATACAAGCAGCAGCACTGTGGTA

TTCGGCGGAGGGACCAAGCTGACCGTCCTAGGG

A positive clone with the right sequence was amplified with the primer as below, and then it was inserted into the prokaryotic expression vector pET32a (Promega Co.).

The reaction condition for PCR was:

The reaction system was 50 μL:

```
Upstream primer for ScFv amplification:
5'-GGATCCCAGGTGCAGCTGCAGGA-3';  (SEQ ID NO: 12)

Downstream primer:
5'-AAGCTTGCTGACCGTCCTAGGG-3';  (SEQ ID NO: 13)
```

10×PCR Buffer ($Mg^{2+}$) 5 μL, dNTP Mixture (2 mM) 5 μL, the upstream and the downstream primers of 1 μL respectively (10 μmol/L), Blendtaq-plus (Promega Co.) 0.5 μL, positive phage antibody clone 1 μL.

Sterilized deionized water was used to fill the system to 50 μL.

The processes for PCR amplification were:

Predenaturing at 94° C. for 4 minutes; denaturing at 94° C. for 45 s; annealing at 54° C. for 40 s; extending at 72° C. for 60 s; and, after 28 cycles, extending at 72° C. for 10 minutes. The reaction products were then separated by 1.2% agarose gel electrophoresis. recovered and purified, to obtain the ScFv fragment by PCR amplification.

Enzyme digestion reaction: the pET32a vector was digested with the double enzymes of BamHI (Takara Co.) and HindIII (Takara Co.), and the fragment of the vector was recovered by digested product recovery kit. The PCR amplified ScFv fragment was digested with the double enzymes of BamHI and HindIII (Takara Corp.), and the fragment of ScFv was recovered by digested product recovery kit.

Ligation reaction system (10 μL): digested product pET32a 1 μL (50 ng/μL); digested product ScFv 5 μL (50 ng); ligation buffer 2 μL; T4 DNA ligase (Promega Co.) 1 μL. Deionized water was added to achieve a final volume of 20 μl. Ligation reaction is conducted overnight at 16° C. E. coli HB2151 (Promega Co.) was transformed by the ligated product. The monoclones were selected and the plasmids thereof were identified by enzymes digestion. Positive clones are conducted to sequencing by Shanghai Biotech Co., and the recombined vector of pET32a-ScFv was constructed.

Example 2

The anti-bFGF humanized ds-Diabody of the present invention is formed based on the VL gene fragment and VH gene fragment encoding the anti-bFGF ScFv prepared in example 1. By overlapping PCR and PCR, a site-directed mutation of amino acid Gly at the site of 100th position of antibody VL and amino acid Gly at the 44th position of antibody VH into Cys is applied, and a covalent disulfide bond was introduced, and in the meanwhile a gene fragment encoding a linker peptide with the amino acid sequence of GGGGS is used to construct the VL-GGGGS-VH gene fragment (with a length of 705 bp). Two expressed VL-GGGGS-VH (with the molecular weight of 49.78 KD) molecules were covalently ligated by disulfide bond to form a dimeric antibody with stable disulfide bond.

Methods for Preparation of Anti-bFGF Humanized Ds-Diabody are as Follows:

1. Preparation of VL-GGGGS-VH (1) The Amino Acid at the Site of 100th Position was Mutated from Gly to Cys by PCR Site-Directed Mutation, and the Gene Fragment of VL-GGGGS was Obtained by Amplification:

Reaction 1): Primer Design:

```
Primer 1:
5'-GCGGCCGCCCAGTCTGTGTTGACGCAGCC-3'; (Not I)
(SEQ ID NO: 5)

Primer 2:
5'-TAGGACGGTCAGCTTGGTCCCACAGCCGAATACCACAGTGC
TGCT-3'; (Cys) (SEQ ID NO: 6)
```

The reaction system (1) was:

10×PCR Buffer (Mg$^{2+}$) 5 μL, dNTP mixture (2 mM 5 μL, primer 1 (10 μmol/L) 1 μL, primer 2 (10 μmol/L) 1 μL, Blendtaq-plus (2.5 U/μL, Promega Co.) 0.5μ pET32a-ScFv recombination vector 1 μL (50 μmol/L), sterilized deionized water 36.5 μL. The total volume was 50 μL.

Procedures of PCR amplification were:

Predenaturing at 94° C. for 2 minutes; denaturing at 94° C. for 30 s; annealing at 63° C. for 30 s; extending at 72° C. for 40 s; and after 30 cycles, extending at 72° C. for 10 minutes. The reaction product was then separated by 1.5% agarose gel electrophoresis, recovered and purified, to obtain the VL in which the amino acid Gly at the 100th position was mutated to Cys.

Reaction 2): Primer Design:

```
Primer 1:
5'-GCGGCCGCCCAGTCTGTGTTGACGCAGCC-3'; (Not I)
(SEQ ID NO: 5)

Primer 3:
5'-CGAGCCACCGCCACCTAGGACGGTCAGCTTGG
TCC-3'; (Linker) (SEQ ID NO: 7)
```

The reaction system (2) was:

10×PCR Buffer (Mg$^{2+}$) 5 μL, dNTP Mixture (2 mM) 5 μL, primer 1 (10 μmol/L) 1 μL, primer 3 (10 μmol/L) 1 μL, Blendtaq-plus (2.5 U/μL) 0.5 μL, template which is the gel recycled product obtained from reaction 1) 1 μL, sterilized deionized water 36.5 μL. The total volume was 50 μL.

Procedures of PCR amplification were:

Predenaturing at 94° C. for 2 minutes; denaturing at 94° C. for 30 s; annealing at 63° C. for 30 s; extending at 72° C. for 40 s; and after 30 cycles extending at 72° C. for 10 minutes. The reaction product was then separated by 1.5% agarose gel electrophoresis, recovered and purified, and the gene fragment VL-GGGGS was obtained.

(2) The Amino Acid at the Site of 44th Position of VH was Site-Directed Mutated from Gly to Cys by PCR, the Gene Fragment VH-GGGGS was Obtained by Amplification.

Reaction 3): Primer Design

```
Primer 4:
5'-GGTGGCGGTGGCTCGCAGGTGCAGCTGCAGGAGTCT-3';
(Linker) (SEQ ID NO: 8)

Primer 5:
5'-CCCACTCCAGACACTTCCCTGGAGCCTGGCGGA-3'; (Cys)
(SEQ ID NO: 9)
```

The reaction system (3) was:

10×PCR Buffer (Mg$^{2+}$) 5 μL, dNTP Mixture (2 mM) 5 μL, primer 4 (10 μmol/L) 1 μL, primer 5 (10 μmol/L) 1 μL, Blendtaq-plus (2.5 U/μL) 0.5 μL, anti-bFGF ScFv plasmid 1 μL, sterilized deionized water 36.5 μL. The total volume was 50 μL.

Procedures of PCR amplification were:

Predenaturing at 94° C. for 2 minutes; denaturing at 94° C. for 30 s; annealing at 62° C. for 30 s; extending at 72° C. for 20 s; and after 30 cycles, extending at 72° C. for 5 minutes. The reaction product was then separated by 1.5% agarose gel electrophoresis, recovered and purified, to obtain a portion of VH-GGGGS.

Reaction 4): Primer Design:

```
Primer 6:
5'-TCCAGGGAAGTGTCTGGAGTGGGTTTCATACAT-3'; (Cys)
(SEQ ID NO: 10)

Primer 7:
5'-GGATCCTCAATGATGATGATGATGGTGTGAGGAGACAGTGACC
AT-3'. (BamHI)(SEQ ID NO: 11)
```

10×PCR Buffer (Mg$^{2+}$) 5 μL, dNTP Mixture (2 mM) 5 μL, primer 6 (10 μmol/L) 1 μL, primer 7 (10 μmol/L) 1 μL, Blendtaq-plus (2.5 U/μL) 0.5 μL, the pET32a-ScFv recombined vector plasmid 1 μL, sterilized deionized water 36.5 μL. The total volume was 50 μL.

Procedures of PCR amplification were:

Predenaturing at 94° C. for 2 minutes; denaturing at 94° C. for 30 s; annealing at 60° C. for 30 s; extending at 72° C. for 30 s; and after 30 cycles, extending at 72° C. for 5 minutes. The reaction product was then separated by 1.5% agarose gel electrophoresis, recovered and purified, to obtain the portion of VH-GGGGS with BamHI sites.

Reaction 5): PCR Splicing and Amplifying Gene Fragment VH-GGGGS.

Overlap PCR Splicing Reaction System (System of 25 μl)

10×PCR Buffer (Mg$^{2+}$) 2.5 μL, dNTP Mixture (2 mM) 2 μL, the product obtained by reaction 3) 5 μL, the product obtained by reaction 4) 5 μL, Blendtaq-plus (2.5 U/μL) 0.5 μL, sterilized deionized water 10 μL.

Procedures of PCR amplification were:

Predenaturing at 94° C. for 2 minutes; denaturing at 94° C. for 30 s; annealing at 60° C. for 30 s; extending at 72° C. for 40 s; and after 7 cycles, extending at 72° C. for 10 minutes.

Gene fragment VH-GGGGS is obtained by PCR amplification. Equal volume of amplification reaction solution was added into the above spliced product (25 μl):

10×PCR Buffer (Mg$^{2+}$) 2.5 μL, dNTP Mixture (2 mM) 4 μL, primer 4 1 μL, primer 7, 1 μL, Blendtaq-plus (2.5 U/μL) 0.5 μL, sterilized deionized water 16 μL.

Procedures of PCR amplification were:
Predenaturing at 94° C. for 2 minutes; denaturing at 94° C. for 30 s; annealing at 60° C. for 30 s; extending at 72° C. for 40 s; and after 30 cycles, extending at 72° C. for 10 minutes. The reaction product was then separated by 1.5% agarose gel electrophoresis, recovered and purified, to obtain the complete VH-GGGGS.

(3) PCR Splicing, Amplifying Gene Fragment of VL-GGGGS-VH

Overlap PCR Splicing Reaction System (System of 25 μL) 10×PCR Buffer ($Mg^{2+}$) 2.5 μL, dNTP Mixture (2 mM) 2 μL, the product obtained by reaction 2) 5 μL, the product obtained by reaction 5) 5 μL, Blendtaq-plus (2.5 U/μL) 0.5 μL, sterilized deionized water 10 μL.

Figure 1:
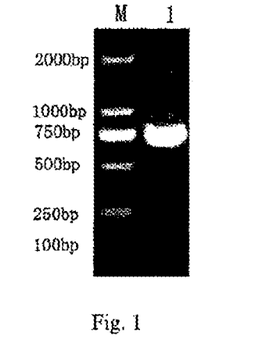
FIG. 1 shows the result of gel electrophoresis of the gene fragment of the anti-bFGF humanized ds-Diabody constructed by site-directed mutation and PCR amplification.

Procedures of PCR amplification were:
Predenaturing at 94° C. for 2 minutes; denaturing at 94° C. for 30 s; annealing at 60° C. for 30 s; extending at 72° C. for 1 minute; and after 7 cycles, extending at 72° C. for 10 minutes. The amplified product was detected by agarose gel electrophoresis, and the results were shown in FIG. 1. The gene fragment of VL-GGGGS-VH fragment obtained could be deduced according to the length of fragment.

2. Construction of the Clone Vector PMD18-T-ds-Diabody and the Recombinant Expression Plasmid p3XFLAG-Myc-CMV-25-ds-Diabody.

(1) Construction of the Clone Vector PMD18-T-ds-Diabody

The gene fragment VL-GGGGS-VH obtained by amplification was ligated to pMD18-T vector (Bao Bioengineering Inc.). Ligation reaction system (10 μL) comprised:

pMD18-T (50 ng/μL) 1 μL, VL-GGGGS-VH fragment 100 ng, Solution I 10 μl. Deionized water was added to reach a final volume of 20 μl;

Ligation was conducted at 16° C. for 8 h, and the ligation reaction product was transformed into the competent cells of *E. coli* DH5α (Bao Bioengineering Inc.), which was then seeded to an $Amp^+$ LB agarose culture plate and kept overnight. The single colonies were selected for amplification, and the plasmid was extracted, identified correctly by Not I and BamH I enzyme digestion reaction. Then sequencing identification was conducted by Sangon Biotech (Shanghai) Co. The results showed that the Dsdiabody gene obtained by mutation was correct, proving that the clone vector was constructed successfully.

(2) Construction of the Expression Vector p3XFLAG-Myc-CMV-25-ds-Diabody.

(1) The clone vector PMD18-T-ds-Diabody and the expression vector p3XFLAG-Myc-CMV-25 were subjected to the double enzyme digestion by Not I and BamH I.

Enzyme digestion system (50 μL):
PMD18-T-ds-Diabody/p3XFLAG-Myc-CMV-25, 1 μg, 10× Buffer K 2.5 μL, BSA 5 μL, Not I (4~12 U/μL) 2 μL, BamH I (8~20 U/μL) 2 μL. Deionized water is added to reach a final volume of 50 μL.

Enzyme digestion was conducted at 37° C. for 8 h. The enzyme digested reaction product was separated by 1.5% agarose gel electrophoresis, recovered and purified, to obtain the expression vector p3XFLAG-Myc-CMV-25 and the VL-GGGGS-VH with Not I and BamH I enzyme digestion sites, respectively.

(2) Ligation of the Gene Fragment VL-GGGGS-VH Obtained from the Enzyme Digestion (1) and the Expression Vector p3XFLAG-Myc-CMV-25 after Enzyme Digestion.

Ligation Reaction System (20 μL):
VL-GGGGS-VH 200 ng, p3XFLAG-Myc-CMV-25, 450 ng, 10× Buffer 2 μl, T4 DNA ligase (350 U/μL) 1 μl. Deionized water was added to reach a final volume of 20 μl.

Figure 2:
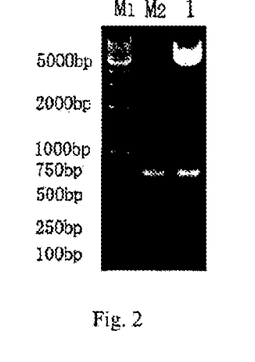
FIG. 2 shows the result of agarose gel electrophoresis of the expression vector p3XFLAG-Myc-CMV-25-ds-Diabody identified by double enzyme digestion.
Figure 3:
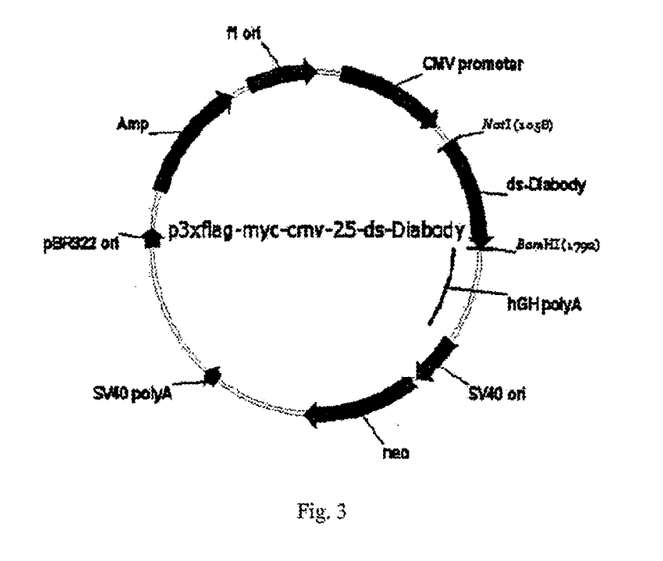
FIG. 3 shows the construction of the expression vector p3XFLAG-Myc-CMV-25-ds-Diabody.

Ligation was conducted at 16° C. for 12 h. The ligation reaction product was transformed into the competent cell of *E. coli* DH5a, which is then seeded to the $Amp^+$ LB agarose culture plate and kept overnight. The single colonies were selected for amplification, and the plasmid was extracted, identified by enzyme digestion of Not I and BamH I. The result showed that the expression vector p3XFLAG-Myc-CMV-25-ds-Diabody was constructed successfully (shown in FIG. 2), and the schematic figure of the structure was shown in FIG. 3.

3. Expression and Western Blot Assay of Anti-bFGF Humanized ds-Diabody.

(1) Expression of Anti-bFGF Humanized ds-Diabody $3 \times 10^6$ human embryonic kidney (HEK 293T) cells (The Institute of Cells of Shanghai, Chinese Academy of Science) were seeded to cell culture plate (100 mm×20 mm), and is cultured at 37° C. with 5% $CO_2$ for 15 hours, with the DMEM culture medium containing a volume percentage of 10% fetal calf serum (FBS). Before transfection, the cell culture medium was replaced by DMEM basic culture medium containing 100 μmol/L chloroquine. 10 μg p3XFLAG-Myc-CMV-25-ds-Diabody was added into 500 μL opti-MEM I low serum culture medium, mixed and then added with 40 μL transfection reagent Fugene HD, After vortex mixing, it is centrifuged at a low speed (800 rpm), and then kept still at room temperature for 15 minutes, then dropped to the cell culture medium, mixed and cultured at 37° C. for 6 hours. The cells were then washed twice with 0.015 mol/L PBS (pH7.4), added with DMEM culture medium containing 10% (v/v) FBS and 4 mmol/L valproic acid, and cultured at 33° C. with 5% $CO_2$. The medium was changed every 64 h, twice in total. The replaced cell culture supernatant was collected for antibody purification.

(2) Western Blot Identification of the Expression Supernatant of the Anti-bFGF Humanized ds-Diabody.

Figure 4:
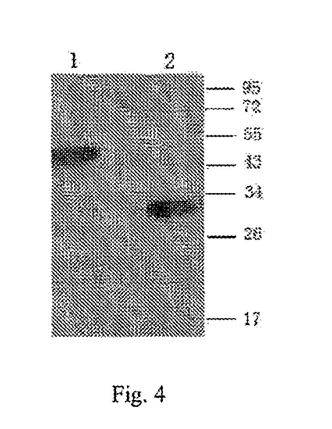
FIG. 4 shows the Western blot assay of the expression supernatant of the cells of the anti-bFGF humanized ds-Diabody that has been subjected to gel electrophoresis SDS-PAGE under reducing condition and non-reducing condition.

15 μL cell expression supernatant was collected, and was subjected to the procedure according to the protocol of molecular clone. The proteins in the supernatant were separated by SDS-PAGE under reducing condition and non-reducing condition, and Western blot identification was conducted. The results (FIG. 4) showed that there was a protein band at 30 kD molecular weight after the SDS-PAGE under reducing condition, and there was a protein band at 50 kD molecular weight after the SDS-PAGE under non-reducing condition, demonstrating that the ds-Diabody was successfully constructed.

4. Purification and SDS-PAGE Assay of the Anti-bFGF Humanized ds-Diabody.

Figure 5:
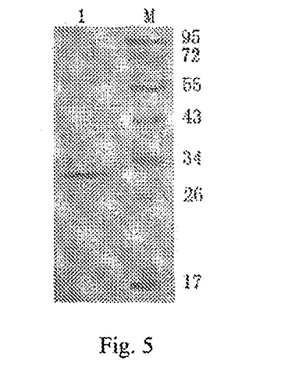
FIG. 5 shows the result of SDS-PAGE gel electrophoresis of the expressed anti-bFGF humanized ds-Diabody that has been purified by Ni Sepharose™ 6 Fast Flow.

The expression supernatant was collected and precipitated using 50% saturated ammonium sulfate, kept still overnight at 4° C., and centrifuged at 8500 rpm for 20 min. Then the supernatant was discarded, and 8 ml PB (sodium phosphate 20 mM, NaCl 0.5M, pH7.4) was added into the precipitation for dissolution. After dialysis with PB and filtration with 0.45 μm filter membrane, purification was conducted using Ni Sepharose™ 6 Fast Flow column. The column was washed with water firstly, equilibrated with equilibration buffer (sodium phosphate 20 mM, NaCl 0.5M, imidazole 5 mM, pH7.4), then loaded with the sample at a flow rate of 250 μl/min, and washed with the balanced buffer (sodium phosphate 20 mM, NaCl 0.5M, imidazole 5 mM, pH7.4). Then PB containing 200 mmol/L imidazole was used to elute impure proteins, and the targeted protein was eluted by PB comprising 300 mmol/L immidazole. At last, the collected protein was ultrafiltrated with 30 KD ultrafiltration tube and was replaced with PBS (0.015 mol/L, pH7.4). The purified product was identified by 12% SDS-PAGE (shown in FIG. 5). The results showed that there was a protein band at 30 kD molecular weight, and the purity of the antibodies reached 95% after purification.

Example 3

Biological activities assay of the anti-bFGF humanized ds-Diabody prepared by the above-mentioned method were shown as below, with the following methods and results:

1. Binding Activity Assay of the Anti-bFGF Humanized Ds-Diabody to the Antigen bFGF by Indirect ELISA.

The recombined humanized bFGF (Sigma-Aldrich Co.) was diluted to 0.5 μg/ml with carbonate buffer solution (0.05 mol/L, pH9.6) to coat ELISA plates at an amount of 100 μL/well, and incubated at 37° C. for 3 h. After discarding the liquid in the well, the plates were washed with PBST (PBS, 0.015 mol/L, pH 7.4, comprising Tween 20 0.05%(v/v)) for three times, blocked with fat-free milk-PBST 5%(wt), added with the ds-Diabody and anti-bFGF ScFv prepared according to example 1 at a certain concentration to achieve an amount of 100 μL/well. Then the plates were incubated at 37° C. for 1 h, washed with PBST for three times, added with 100 μL/well diluted anti-His-tag mouse monoclonal antibody 1:2000 (v/v) (sigma-aldrich Co.), incubated at 37° C. for 1 h, washed with PBS-T for three times again, and then added with diluted HRP marked goat anti-mouse polyclonal antibody (1:8000 (v/v) (sigma-aldrich Co.), and incubated at 37° C. for 0.5 h. After that, the plates were washed with PBS-T for 5 times, stained by TMB and detected at A450. Meanwhile, PBS was used as a negative control.

Figure 6:
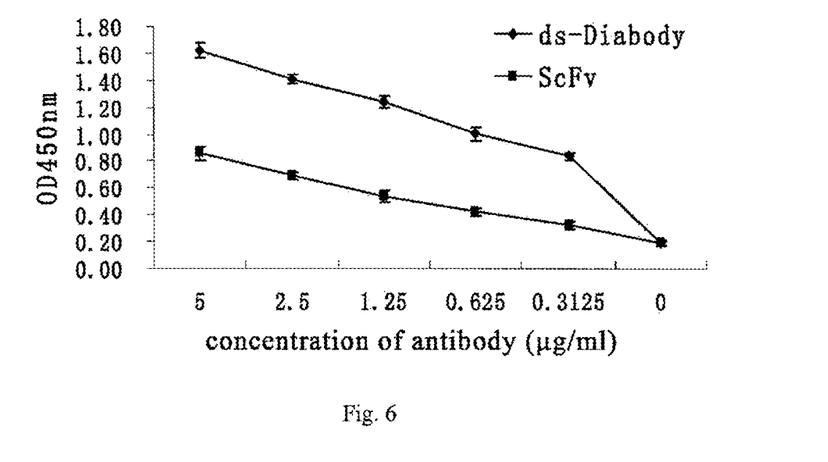
FIG. 6 shows the binding activity of the anti-bFGF humanized ds-Diabody to antigen bFGF tested by indirect ELISA.

The result was shown in FIG. 6. Compared with ScFv, ds-Diabody presented a better specific binding activity and high affinity to antigen bFGF.

2. Measurement of Serum Stability In Vitro of the Anti-bFGF Humanized ds-Diabody.

Purified ds-Diabody and ScFv at a certain concentration were dissolved in PBS with 0.2% (w/v) human serum albumin (HAS), incubated at 37° C. for 0 h, 1 h, 2 h, 4 h, 8 h, 12 h, 24 h, 48 h and 72 h. The incubated antigens were sampled at each time point, added into the ELISA plates at an amount of 100 μl/well, wherein said plate was coated with 50 ng/well bFGF. Then incubation was conducted at 37° C. for 1 h. The plates were washed with PBST for three times, added with 100 μL/well diluted anti-His-tag mouse monoclonal antibody (1:20000 (v/v)), incubated at 37° C. for 1 h and then washed with PBS-T for three times. Then diluted HRP conjugated goat anti-mouse polyclonal antibody (1:8000 (v/v)) was added at an amount of 100 μL/well. The plates was then incubated at 37° C. for 0.5 h, washed with PBS-T for 5 times, stained by TMB and detected at A450.

Figure 7:
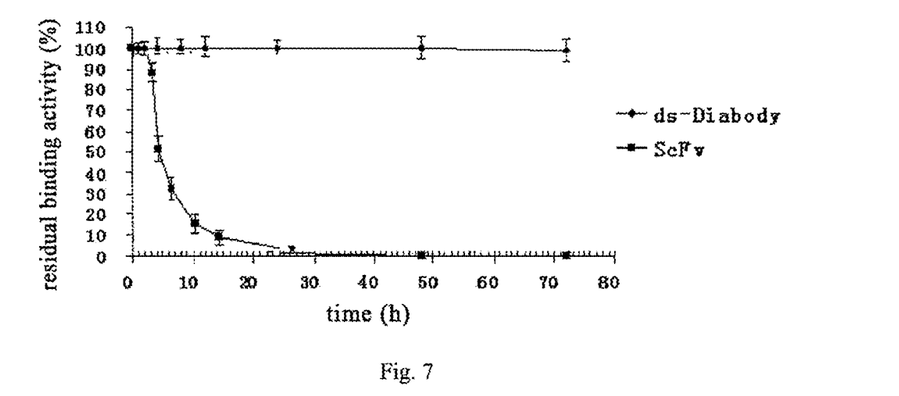
FIG. 7 shows the stability of the anti-bFGF humanized ds-Diabody.

The results were shown in FIG. 7, the activity of ScFv began to decrease after 1 h of incubation in the PBS comprising 0.2% of HAS at 37° C., and the activity left only about ½ after 2 h. After 24 h, the activity was totally lost. For ds-Diabody, the activity maintained without any obvious changes after 72 h of incubation. The results showed the anti-bFGF humanized ds-Diabody is of great stability.

Preferred embodiments of the present invention are shown above. However, the embodiments of the present invention are not limited to the above examples. Any amendments, modifications, replacements, combinations, simplifications that are made without deviating from the spirit and mechanism of the present invention should be considered as the equivalent substitution, and should be included in the extent of protection of the present invention.

What is claimed is:

1. A nucleic acid comprising the sequence of SEQ ID NO:2.

2. A humanized anti-bFGF scFv antibody encoded by the nucleic acid of claim 1, which comprises the sequence of SEQ ID NO:1.

3. An anti-bFGF ds-Diabody comprising two humanized anti-bFGF scFv antibodies of claim 2.

4. The anti-bFGF ds-Diabody of claim 3, wherein the two humanized anti-bFGF scFv antibodies are linked by disulfide bonds.

5. A method for preparing an anti-bFGF ds-Diabody linked by disulfide bonds comprising cloning the nucleic acid of claim 1 into a eukaryotic expression vector, transfecting the expression vector into human embryonic kidney (HEK) cells, culturing the HEK cells to express the encoded humanized anti-bFGF scFv antibodies that will further form the anti-bFGF ds-Diabody, and purifying the disulfide bond stabilized ds-Diabody.

6. The method of claim 5, wherein the expression vector is p3XFLAG-Myc-CMV-25.

* * * * *